(12) United States Patent
Newsome

(10) Patent No.: US 7,151,960 B1
(45) Date of Patent: Dec. 19, 2006

(54) DILATION ENHANCER WITH PRE-MEDIATED CONTACT LENSES

(76) Inventor: David A. Newsome, 1701 Oriole, New Orleans, LA (US) 70122

( * ) Notice: Subject to any disclaimer, the term of this patent is extended or adjusted under 35 U.S.C. 154(b) by 1114 days.

(21) Appl. No.: 09/634,054

(22) Filed: Aug. 8, 2000

Related U.S. Application Data

(63) Continuation-in-part of application No. 09/160,106, filed on Sep. 24, 1998, now Pat. No. 6,101,411.

(51) Int. Cl.
  *A61N 1/30* (2006.01)
(52) U.S. Cl. .................................................... 604/20
(58) Field of Classification Search ............... 604/20, 604/294–298, 300, 301
  See application file for complete search history.

(56) References Cited

U.S. PATENT DOCUMENTS

| | | | |
|---|---|---|---|
| 2,525,381 A | 10/1950 | Tower | |
| 4,109,648 A | 8/1978 | Larke et al. | 128/2.06 E |
| 4,564,016 A | 1/1986 | Maurice et al. | 128/645 |
| 5,174,304 A | 12/1992 | Latina et al. | |
| 5,192,665 A | 3/1993 | Salonen | |
| 5,498,521 A | 3/1996 | Dryja et al. | |
| 5,522,864 A | 6/1996 | Wallace et al. | |
| 6,154,671 A * | 11/2000 | Parel et al. | 604/20 |
| 6,312,393 B1 * | 11/2001 | Abreu | 600/558 |
| 6,319,240 B1 * | 11/2001 | Beck | 604/20 |

FOREIGN PATENT DOCUMENTS

| | | |
|---|---|---|
| DE | 1489708 | 5/1969 |
| EP | 325201 | 1/1989 |
| FR | 641745 | 8/1928 |

OTHER PUBLICATIONS

Behar-Cohen, Francine F., et al., "Iontophoresis of Dexamethasone in the Treatment of Endotoxin-Induced-Uveitis in Rats", *Exp. Eye Res.*, (1997) 65, 533-545.
Bradshaw, C.M., et al., "A Procedure for Comparing the Mobilities of Unlabeled Drugs Used in Microelectrophoresis Experiments", *Journal of Pharmacological Methods*, 5, 67-73 (1981).
McBrien, Neville A., et al., "Experimental Myopia in a Diurnal Mammal (*Sciurus carolinensis*) With No Accommadative Ability", *Journal of Physiology*, (1993), 469, pp. 427-441.
Pirch, James H., et al., "A role for acetylcholine in conditioning-related responses of rat frontal cortex neurons: microintophoretic evidence", *Brain Research*, 586 (1992) 19-26.
Sarraf, David, et al., "The role of iontophoresis in ocular drug delivery", *Journal of Oculat Pharmacology*, vol. 10, No. 1: 69-81 (1994).
Yoshizumi, Marc O., et al., "Determination of Ocular Toxicity in Multiple Applications of Foscarnet Iontophoresis", *Journal of Ocular Pharmacology and Therapeutics*, (1997), 13:6, pp. 529-536.

\* cited by examiner

*Primary Examiner*—Michael J. Hayes
(74) *Attorney, Agent, or Firm*—Garvey, Smith, Nehrbass & North, L.L.C.; Seth M. Nehrbass

(57) ABSTRACT

A contact lens with a conductive outer shell (one electrode of a two-electrode electrophoresis device) and a preferably soft, preferably disposable contact lens for contacting a patient's eye, assists in delivering dilation drops or other medicaments to a patient's eye. Advantageously, the lens is used with a relatively small hand-held power source. Electrophoresis can be used to help deliver dilation drops more rapidly, regardless of the delivery apparatus used for the electrophoresis.

8 Claims, 4 Drawing Sheets

DILATION ENHANCER WITH PRE-MEDIATED CONTACT LENSES

CROSS-REFERENCE TO RELATED APPLICATIONS

This is a continuation-in-part of U.S. patent application Ser. No. 09/160,106, filed 24 Sep. 1998, now U.S. Pat. No. 6,101,411, which is incorporated herein by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to pupil dilation and constriction procedures. More particularly, the present invention relates to a method and apparatus for using electrophoresis to deliver pupil dilation and constriction agents.

2. General Background of the Invention

Every individual should have at least one dilated eye examination every 2–3 years in adulthood. Many individuals with various eye problems such as macular degeneration, diabetes, threat of detached retina or history of detached retina as well as many other conditions require repeated dilated eye examinations. Dilated eye examinations typically require patients to wait several minutes after application of a dilator drug before the eye is sufficiently dilated for a dilated eye examination to occur.

Electrophoresis is an electrochemical process in which colloidal particles or molecules with a net electric charge migrate in a solution under the influence of an electric current. It is also sometimes called iontophoresis or cataphoresis. Electrophoresis is sometimes used now by others to deliver vitamins (such as Vitamin C) and antibiotics efficiently.

The present inventor understands that National Public Radio recently reported that tracers placed on tsetse flies and honey bees were powered with light-power-driven transmitters.

The following patents are incorporated herein by reference:

| U.S. Pat. Nos.: | 5,498,521 | 5,192,665 | 5,522,864 |
|---|---|---|---|
| | 5,174,304 | 2,525,381; | |

EP325,201; Fr. 641,745; Germ. 1489708.

U.S. Pat. No. 2,525,381 discloses a contact lens type electrode holder. This electrode holder is used during ionic medication treatment of a patient's eye. The electrode itself has a relatively small surface area. The patent mentions "penicillin or other medicaments".

U.S. Pat. Nos. 5,174,304 and 5,222,864, Fr. Pat. No. 641,745, Germ. Pat. No. 1,489,708, and EP Pat. Office Publication No. 325,201 disclose electrodes for contacting eyeballs.

U.S. Pat. No. 5,498,521 discloses the use of a contact lens electrode placed on a topically anesthetized cornea after dilation of the pupils (see column 17, lines 13–16).

Also incorporated by reference are the following references:

Sarraf, David, et al., "The role of iontophoresis in ocular drug delivery", *Journal of Ocular Pharmacology*, vol. 10, no. 1: 69–81 (1994);

Pirch, James H., et al., "A role for acetylcholine in conditioning-related responses of rat frontal cortex neurons: microintophoretic evidence", *Brain Research*, 586 (1992) 19–26;

Behar-Cohen, Francine F., et al., "Iontophoresis of Dexamethasone in the Treatment of Endotoxin-Induced-Uveitis in Rats", *Exp. Eye Res.*, (1997) 65, 533–545;

Yoshizumi, Marc O., et al., "Determination of Ocular Toxicity in Multiple Applications of Foscarnet Iontophoresis", *Journal of Ocular Pharmacology and Therapeutics*, (1997), 13:6, pp. 529–536;

Bradshaw, C. M., et al., "A Procedure for Comparing the Mobilities of Unlabeled Drugs Used in Microelectrophoresis Experiments", *Journal of Pharmacological Methods*, 5, 67–73 (1981);

McBrien, Neville A., et al., "Experimental Myopia in a Diurnal Mammal (*Sciurus Carolinensis*) With No Accommodative Ability", *Journal of Physiology*, (1993), 469, pp. 427–441.

BRIEF SUMMARY OF THE INVENTION

The apparatus of the present invention solves the problems confronted in the art in a simple and straightforward manner. What is provided is a dilation enhancer apparatus and method.

The dilation enhancer apparatus of the present invention is a hand held electrophoretic device using a contact lens type delivery system to provide rapid clinically useful dilation of the pupil of the eye. Other clinical applications may be useful.

The present invention comprises a contact lens with a conductive outer shell (one electrode of a two-electrode electrophoresis device) and a preferably soft, preferably disposable contact lens (made of a material such as polyfilcon, e.g. ocufilcon) for contacting a patient's eye. The present invention also comprises apparatus including the contact lens with the conductive outer shell and a relatively small hand-held power source. The present invention also comprises a method of using electrophoresis to help deliver dilation drops more rapidly, regardless of the means used for the electrophoresis.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

PARTS LIST

Figure 1:
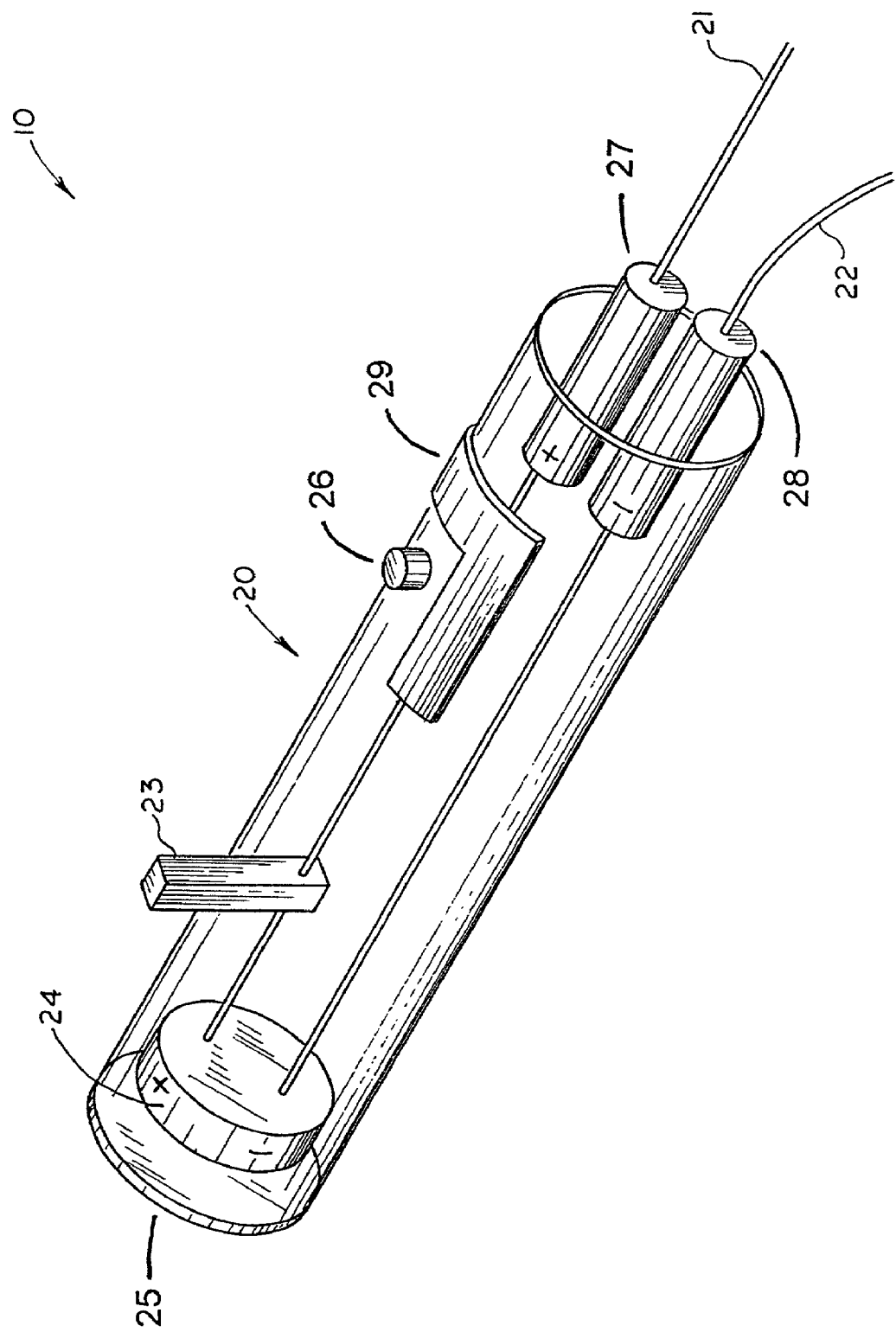
FIG. 1 is a perspective view of the preferred embodiment of the power supply apparatus of the present invention.
Figure 2:
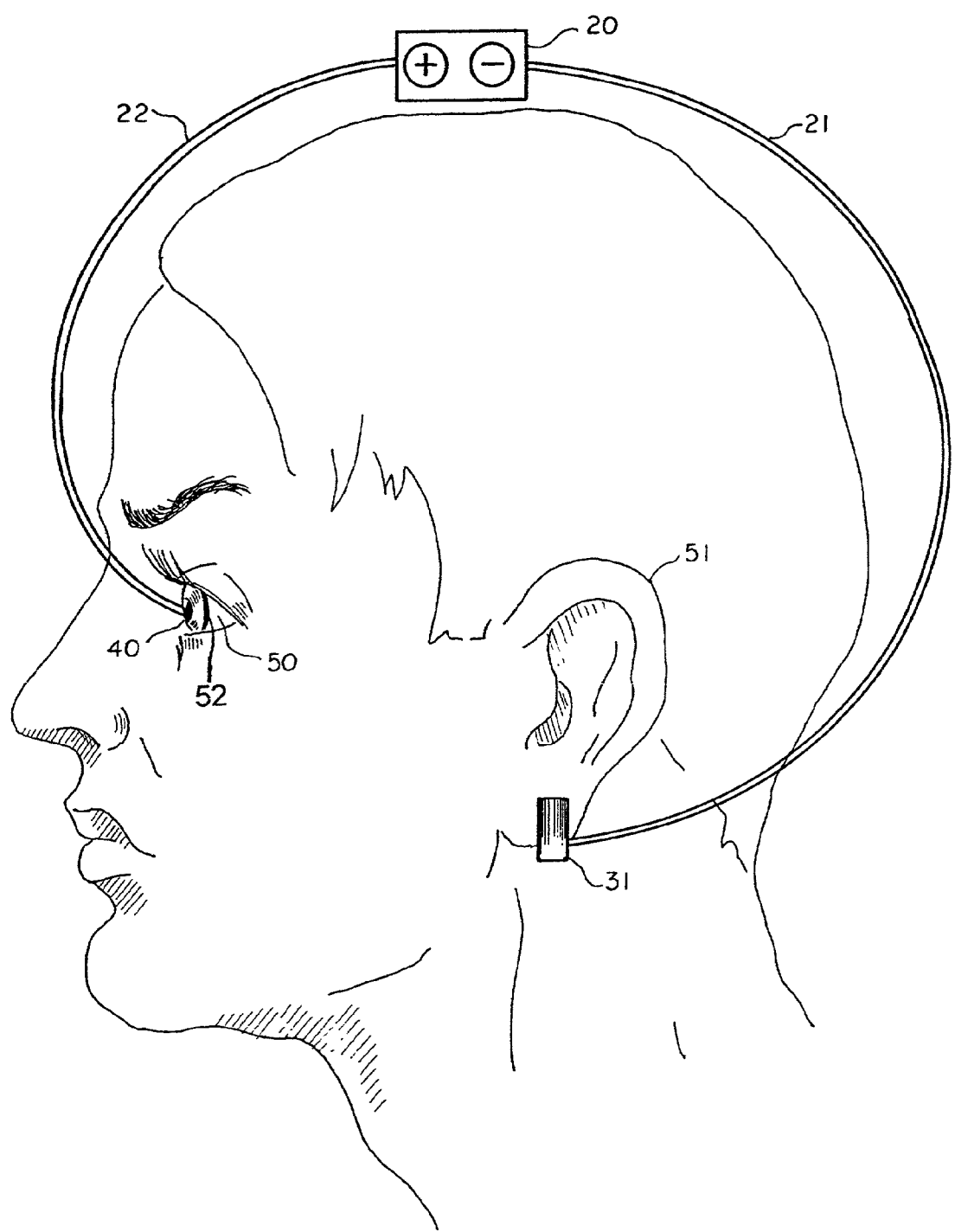
FIG. 2 shows the preferred embodiment of the apparatus of the present invention in use on a patient.
Figure 3A:
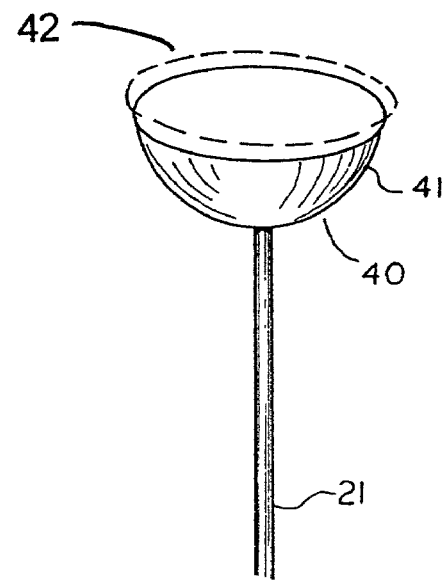
FIG. 3A is a side view of the preferred embodiment of the contact lens electrode apparatus of the present invention.
Figure 3B:
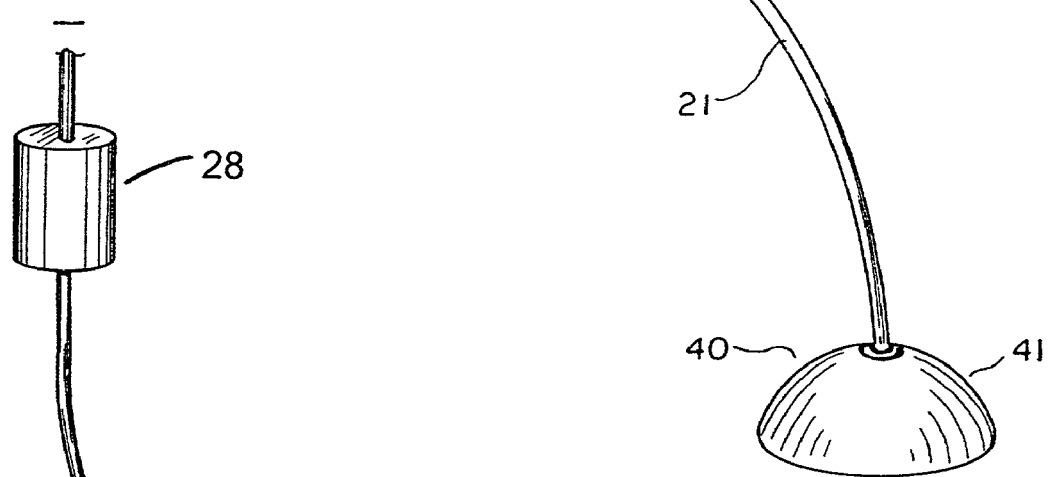
FIG. 3B is a top view of the preferred embodiment of the contact lens electrode apparatus of the present invention.
Figure 3:
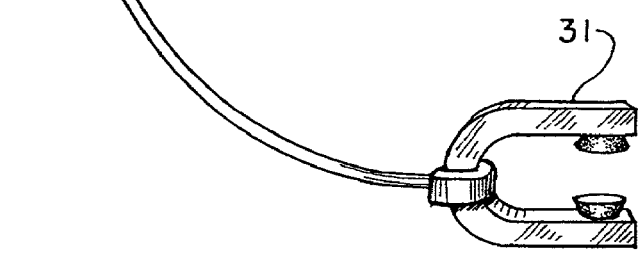
FIG. 3 is a side view of the preferred embodiment of the earlobe clamp apparatus of the present invention.

| | |
|---|---|
| 10 | dilation enhancer of the present invention |
| 20 | hand-held iontophoretic power source (dilation enhancer power supply) |
| 21 | positive wire electrode (to eye) |
| 22 | negative wire electrode (to ear) |
| 23 | "on/off" switch (starter, reset) |
| 24 | battery with 1 milliamp output |
| 25 | battery access cover |
| 26 | "on" light and elapsed timer |
| 27 | positive receptacle |
| 28 | negative receptacle |
| 29 | timer with automatic one minute shutoff |
| 31 | reference electrode (conductive comfortable earlobe clamp with conductive padding) |
| 40 | conductive composite contact lens structure |
| 41 | conductive shell preferably made of metal or other suitable material (such as plastic) (reusable, sterilizable) |
| 42 | preferably disposable soft contact lens (polymer type) |
| 50 | patient's eye |
| 51 | patient's ear |
| 52 | patient's limbus |
| 54 | patient's cornea |
| 55 | patient's sclera |
| 56 | patient's iris |
| 110 | dilation enhancer of the present invention |
| 120 | flexible light-activated iontophoretic power source (dilation enhancer power supply - commercially available) |
| 121 | positive electrode |
| 122 | negative electrode |
| 140 | conductive composite contact lens structure |
| 141 | photovoltaic contact lens (preferably made of polymacon-type material or other suitable material) (preferably reusable and sterilizable) |
| 142 | preferably disposable soft contact lens (polymer type) presoaked with a dilation drug or dilation reversal drug |

DETAILED DESCRIPTION OF THE INVENTION

The present technique consists of topically applying one or more eye drops of particular compounds that either stimulate the dilator muscle of the iris or paralyze the constricting sphincter muscle of the iris to produce pupillary dilation. The usual time is at least 20 minutes and may be considerably longer in order to achieve clinically useful dilation to promote examination.

The dilation enhancer 10 of the present invention uses a novel contact delivery system operated through a hand-held iontophoretic power source 20 to deliver efficacious amounts of dilating drugs across the cornea of the eye 50 to bathe the iris of the eye 50 very rapidly achieving a rapid, complete, clinically useful dilation.

The same technique can be used with other compounds to produce a reversal of the dilation much more rapidly than by the prior technique of topical drop application.

Description of the Device:

In the present invention, iontophoresis employs a current flow at low amperage from a positive electrode across tissues enhanced by the presence of a reference electrode 31 clamped onto the patient's ear 51.

The power supply 20 is constructed with internal regulation such that there is a steady output of a predetermined (preferably one milliamp) current. The current is delivered through wire electrodes 21, 22 to a conductive contact lens 40. Conductive composite contact lens structure 40 includes a conductive shell 41 preferably made of metal or other suitable material (such as plastic) and preferably reusable and sterilizable, having a diameter appropriate for a patient's eye (such as about 10 mm) and a preferably disposable soft contact lens 42 which fits in the conductive shell 41 and has a similar diameter (such as about 11 mm).

The hand held device has an "on/off" switch 23. It is preferably battery 24 powered.

Example of Operation of the Device:

After the patient is informed of what sensations to expect, a single topical anesthetic drop is applied to each eye.

The electrophoretic composite contact lens structure 40 is charged with one drop each of 2.5% Phenylephrine and 1% Tropicamide. The composite contact lens structure 40 is applied corneal surface down to the cornea with the patient's lids supported open. The current is switched on and the composite contact lens structure 40 left in place for a period of 90 seconds. At the end of the 90 seconds, the composite contact lens structure 40 is removed. The eye is observed for another 60 seconds and should show substantial if not full dilation. If less than optimal dilation is achieved, the process can be repeated.

The same sequence is carried out for the other eye.

At the end of examination, a dilation reversing drop is used to charge the contact lens corneal side. Electrophoresis is again switched on for a period of 90 seconds. The patient then receives an artificial tear drop and should be comfortably ready to be discharged from the office or other venue.

Possible Risks and Benefits:

Using the current of one milliamp, no corneal surface or stroma problems have been noted.

The direction of the current across the cornea and the wide spread area of application of the current minimizes the likelihood of any tissue damage and keeps the electrophoretic current away from other tissues such as ciliary body and retina.

The major benefit of the device is allowing the patient to undergo a dilated examination within a very short time after concluding any undilated examination, eliminating the protracted wait for dilation to occur. The technique also provides wider dilation than is achievable even by repeated drop application.

The apparatus of the present invention can also be used for corneal antibiotic or other drug delivery.

The device of the present invention may also be useful for preliminary testing of responsiveness to antiocular hypotensive drugs, currently now a laborious process for practitioner and patient involving repeat visits spaced out over weeks of time.

Experiments to prove efficacy of the present invention:

Purpose:

To determine the pupillary dilation efficacy of Iontophoresis vs. Topical Application of: a) Phenylephrine 2.5% and b) Tropicamide 1%. Also to determine the dilation reversal efficacy of RevEyes and Pilocarpine 2%.

Methods:

Experiment I—4 Rabbits Used
1) Drug added by applying one drop to right eye then observing pupillary changes at 0, 2 minutes, 5 minutes and 10 minutes.
2) Drug to other eye added by electrophoresis at 4 mA for 2 minutes. Pupillary changes monitored as above.

Experiment II—4 Rabbits Used
1) One drop added and pupillary changes monitored at 0, 2 minutes, 5 minutes and 10 minutes.
2) To the other eye Phenylephrine electrophoresis at 1 mA for 2 minutes. Pupillary changes monitored as above.

Experiment III—4 Rabbits Used
1) Both eyes subjected to electrophoresis of Phenylephrine or Tropicamide at 1 mA for 2 minutes.
A) One eye received 1 drop of RevEyes or Pilocarpine and pupillary changes monitored.
B) Other eye electrophoresis of RevEyes or Pilocarpine at 1 mA for 2 minutes.

NOTE: Addition of RevEyes or Pilocarpine by drop; small changes seen at 10 minutes; at 20 minutes pupils were more nearly normal by still about 6 mm ("normal" is about 4 mm).

Pupil dilation was observed at 2 minutes with electrophoresis of Phenylephrine at 4 mA or 1 mA. The 1 mA was most comfortable for the animal. There was no increase in heavy breathing or heart rate as with 4 mA. Addition of drop application did not fully dilate pupils until the 10 minute time point and pupil was still not fully dilated until 20 minutes.

| | Pupil diameter (mm) at: | | | | |
| --- | --- | --- | --- | --- | --- |
| | 0 time | 2 min. | 5 min. | 10 min. | 20 min. |
| 2.5% Phenylephrine | | | | | |
| Drop | 4 | 4 | 5 | 8 | |
| Electro. | 4 | 8 | 8 | 10 | |
| RevEyes | | | | | |
| Drop | 9 | 9 | 9 | 9 | 9 |
| Electro. | 10 | 9 | 9 | 8 | 6 |

It may be possible to use wireless technology to produce the current used in the present invention. The advantage of doing so would be in minimizing the wires around the patients' eyes. Apparatus 110 uses wireless technology to produce the current used in the present invention.

Figure 4:
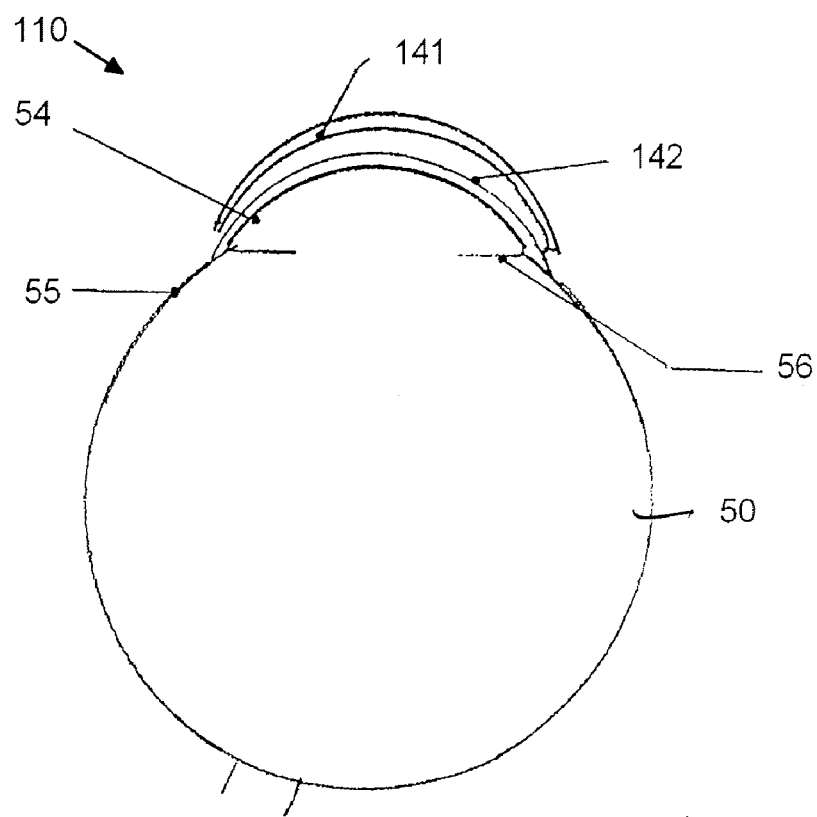
FIG. 4 is a cross-section of a light-driven iontophoretic unit with drug carrying soft contact lens placed on a patient's eye (in actual use the photovoltaic contact lens 141 would touch the soft contact lens 142)
Figure 5:
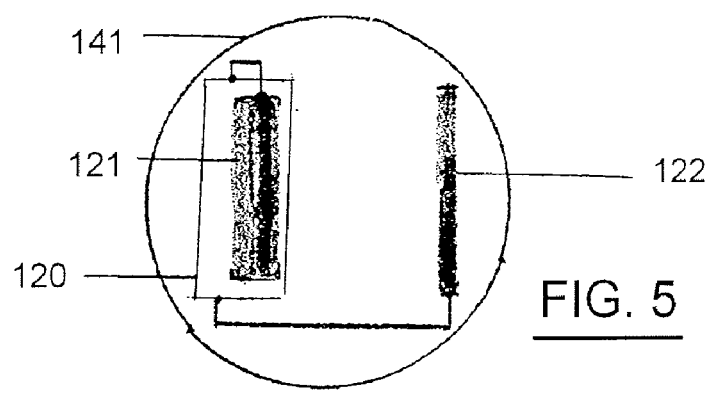
FIG. 5 is a top view of a light-driven iontophoretic unit with drug carrying soft contact lens.
Figure 6:
FIG. 6 is a cross-section of a light-driven iontophoretic unit with drug carrying soft contact lens.

FIG. 4 shows the patient's eye 50, which includes the limbus 52, cornea 54, sclera 55, and iris 56. Dilation enhancer apparatus 110, shown in FIG. 4 on the eye 50, includes a conductive composite contact lens structure 140, which in turn includes a photovoltaic contact lens 141 (preferably made of polymacon-type material or other suitable material (and preferably reusable, sterilizable)) and a preferably disposable soft contact lens 142 (polymer type), preferably presoaked with a dilation drug or dilation reversal drug. Photovoltaic contact lens 141 includes thereon or therein a flexible light-activated iontophoretic power source 120 (dilation enhancer power supply—commercially available). Power source 120 provides power to a positive electrode 121 on lens 141 and to a negative electrode 122 on lens 141.

In practice, two photovoltaic contact lenses 141, each having thereon or therein a flexible light-activated iontophoretic power source 120, a positive electrode 121, and a negative electrode 122, are each provided with a lens 142 presoaked with a dilation drug. The apparatus 110 is then placed on a patient's eyes and then light is shined on the power source 120 for a predetermined period of time (such as 30–60 seconds). This causes the patient's pupils to dilate.

After the patient has been examined, the process is repeated, but each lens 142 in this case is presoaked with a dilation reversal drug.

The contact lenses 142 can be standard soft contact lens material lenses (not prescription) soaked with the appropriate drug, one to make the pupil bigger and one to make the pupil smaller.

Power source 120 can be light-power-driven electrical wafers (which could be reusable).

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. An apparatus for performing electrophoresis on a patient's eye comprising:
   a) a composite contact lens structure that comprises an outer shell having a concave surface and a convex surface;
   b) a disposable lens member that removably fits the shell at the concavity; and
   c) the convex portion of the shell carrying an electrode for transmitting electrical current to the shell and lens member;
   a light-activated power source for providing electricity to the electrode.

2. The apparatus of claim 1 wherein the lens member is soft.

3. The apparatus of claim 2 wherein the lens member is made of polyfilcon.

4. The apparatus of claim 1, wherein the lens member is pre-medicated with a dilator drug or dilator reversal drug.

5. An apparatus for performing electrophoresis on a patient's eye comprising:
   a) a composite contact lens structure that comprises an outer shell having a concave surface and a convex surface;
   b) a disposable lens member that removably fits the shell at the concavity; and
   c) the convex portion of the shell carrying an electrode for transmitting electrical current to the shell and lens member;
   a light-activated power source for providing electricity to the electrode,
   wherein the light-activated power source is on or in the shell.

6. The apparatus of claim 5 wherein the lens member is soft.

7. The apparatus of claim 5 wherein the lens member is made of polyfilcon.

8. The apparatus of claim 5, wherein the lens member is pre-medicated with a dilator drug or dilator reversal drug.

* * * * *